US009848817B2

United States Patent
Torisawa et al.

(10) Patent No.: US 9,848,817 B2
(45) Date of Patent: Dec. 26, 2017

(54) GAS SUPPLY APPARATUS

(71) Applicants: FUJIFILM Corporation, Tokyo (JP); OSAKA UNIVERSITY, Suita-shi, Osaka (JP)

(72) Inventors: Nobuyuki Torisawa, Ashigarakami-gun (JP); Kentaro Hayashi, Ashigarakami-gun (JP); Manabu Miyamoto, Ashigarakami-gun (JP); Kiyokazu Nakajima, Suita (JP)

(73) Assignees: FUJIFILM Corporation, Tokyo (JP); OSAKA UNIVERSITY, Suita (JP)

( * ) Notice: Subject to any disclaimer, the term of this patent is extended or adjusted under 35 U.S.C. 154(b) by 132 days.

(21) Appl. No.: 14/487,601

(22) Filed: Sep. 16, 2014

(65) Prior Publication Data

US 2015/0080757 A1 Mar. 19, 2015

(30) Foreign Application Priority Data

Sep. 18, 2013 (JP) .................................. 2013-193153

(51) Int. Cl.
*A61M 13/00* (2006.01)
*A61B 1/015* (2006.01)
(Continued)

(52) U.S. Cl.
CPC ............ *A61B 5/4255* (2013.01); *A61B 1/015* (2013.01); *A61B 1/31* (2013.01); *A61B 5/03* (2013.01); *A61M 13/003* (2013.01)

(58) Field of Classification Search
CPC ................................ A61B 5/4255; A61B 5/03
See application file for complete search history.

(56) References Cited

U.S. PATENT DOCUMENTS 6,626,847 B1 * 9/2003 Sjovall ............... A61B 5/04884
600/547
2005/0222535 A1 * 10/2005 Uesugi ............... A61B 1/00039
604/26
(Continued)

FOREIGN PATENT DOCUMENTS

| CN | 102697450 A | 10/2012 |
| EP | 2505123 A1 | 10/2012 |

(Continued)

OTHER PUBLICATIONS

Extended European Search Report for European Application No. 14184708.7, dated Jan. 28, 2015.
(Continued)

*Primary Examiner* — Sean Dougherty
(74) *Attorney, Agent, or Firm* — Birch, Stewart, Kolasch & Birch, LLP

(57) ABSTRACT

A gas supply apparatus includes: a gas supply conduit for supplying a gas to a digestive tract; a pressure detecting device which detects a pressure in the digestive tract; a flow regulating device which regulates a gas amount supplied from the gas supply source to the digestive tract via the gas supply conduit; a first control device which controls the flow regulating device according to a result detected by the pressure detecting device to supply the gas into the digestive tract so that the pressure inside the digestive tract becomes a set pressure; a second control device which controls the flow regulating device to supply a fixed gas amount into the digestive tract; and a gas supply mode switching device which switches between gas supply modes including a mode for executing control by the first control device and a mode for executing control by the second control device.

10 Claims, 15 Drawing Sheets

(51) Int. Cl.
*A61B 1/31* (2006.01)
*A61B 5/00* (2006.01)
*A61B 5/03* (2006.01)

(56) References Cited

U.S. PATENT DOCUMENTS

2010/0228100 A1* 9/2010 Vining .................. A61B 5/036
                                                              600/300
2013/0303852 A1  11/2013 Hiraga et al.

FOREIGN PATENT DOCUMENTS

| | | | |
|---|---|---|---|
| JP | 2007-75518 A | | 3/2007 |
| JP | 2015058120 A | * | 3/2015 ............. A61B 1/015 |
| KR | 10-2012-0015598 A | | 2/2012 |
| WO | WO 2013/099507 A1 | | 7/2013 |

OTHER PUBLICATIONS

Chinese Office Action and Search Report for Chinese Application No. 201410472166.3, dated Dec. 29, 2016, with an English translation.
Chinese Office Action issued in Chinese Application No. 201410472166.3, dated May 24, 2017, with English translation.

* cited by examiner

GAS SUPPLY APPARATUS

CROSS-REFERENCE TO RELATED APPLICATIONS

The patent application claims priority under 35 U.S.C. §119 to Japanese Patent Application No. 2013-193153, filed on Sep. 18, 2013. Each of the above application(s) is hereby expressly incorporated by reference, in its entirety, into the present application.

BACKGROUND OF THE INVENTION

Field of the Invention

The present invention relates to gas supply apparatuses, and particularly to a gas supply apparatus capable of performing functional tests of the digestive tract such as tests for functional dyspepsia (FD) and irritable bowel syndrome (IBS).

Description of the Related Art

It is conventionally known that as one of functional tests for the digestive tract, barostat testing is used for measuring an elastic relaxation response disorder as a disorder of digestive tract motility, which is one of conditions of functional dyspepsia (FD). The barostat testing involves the insertion of a barostat balloon (thin bag made of polyethylene) into a digestive tract such as an intestine and a stomach (stomach fundus in the case of FD) so as to measure a capacity, pressure and compliance of the balloon under computer control. The barostat testing offers an advantage that a digestive tract sensation can be quantitatively evaluated by giving a constant low pressure to the digestive tract.

However, the barostat testing accompanies pain and requires a special instrument. Thus, in recent years, a simpler drink test (indirect evaluation method for evaluating how much a nutritional tonic or water can be taken) is also performed instead of the barostat testing. This drink test, although it is very simple, disadvantageously presents a problem that making a detailed evaluation is difficult.

As described above, conventional functional tests for the digestive tract are inadequate in making a diagnosis of functional dyspepsia (FD) and irritable bowel syndrome (IBS) easily and in detail. Thus, development of an art for dealing with this is desired.

On the other hand, when an endoscope is used to perform an examination or give a treatment, gas is supplied into the body cavity (such as abdominal cavity) of a patient via a gas supply conduit provided on the endoscope so as to ensure the vision of the endoscope and the operation area of a treatment tool. Although air has been mainly used until now as a gas supplied to the body cavity, carbon dioxide ($CO_2$ gas) is increasingly used in recent years. Since carbon dioxide has favorable bioabsorbability, damage suffered by the examinee is less. Consequently, carbon dioxide is increasingly used as a gas supply source.

A gas supply apparatus on which a carbon dioxide-filled gas cylinder is installed is used to supply carbon dioxide into a body cavity. The gas supply apparatus is detachably connected to the gas supply conduit of an endoscope so as to supply pressure-reduced carbon dioxide from the carbon dioxide cylinder.

For example, Japanese Patent Application Laid-Open No. 2007-075518 discloses a gas supply apparatus having a plurality of gas supply modes. The gas supply apparatus includes gas supply modes for abdominal cavities and for subcutaneous spaces, determines whether a surgical instrument which supplies gas is for abdominal cavities or for subcutaneous spaces, switches to a gas supply mode according to the determined result, and controls over supplying a predetermined gas having a pressure and a flow rate in response to the switched gas supply mode. This eliminates the need to manually switch between gas supply settings for abdominal cavities and for subcutaneous spaces depending on the surgical procedure and simplified switching enables the prevention of handling errors.

SUMMARY OF THE INVENTION

However, Japanese Patent Application Laid-Open No. 2007-075518 only discloses a gas supply apparatus used for ensuring the vision of the endoscope and the operation area of the treatment tool, and there is no description of suggesting application to functional tests of the digestive tract and no indication of usefulness as an apparatus for functional tests of the digestive tract.

In view of the circumstances described above, an object of the present invention is to provide a gas supply apparatus capable of performing, easily and in detail, functional tests of the digestive tract such as tests for functional dyspepsia (FD) and irritable bowel syndrome (IBS).

In order to achieve the above-mentioned object, a gas supply apparatus according to an aspect of the present invention includes: a gas supply conduit communicating with a gas supply source to supply a gas to a digestive tract inside a subject; a pressure detecting device which detects a pressure in the digestive tract; a flow regulating device which regulates an amount of the gas supplied from the gas supply source to the digestive tract via the gas supply conduit; a first control device which controls the flow regulating device according to a result detected by the pressure detecting device to supply the gas into the digestive tract so that the pressure inside the digestive tract becomes a set pressure; a second control device which controls the flow regulating device according to a capacity of the digestive tract to supply a fixed amount of the gas into the digestive tract, the fixed amount being small enough relative to the capacity of the digestive tract; and a gas supply mode switching device which switches between a plurality of gas supply modes including a first gas supply mode for executing control by the first control device and a second gas supply mode for executing control by the second control device.

According to the aspect of the present invention, the gas supply apparatus includes a gas supply mode of supplying gas in a fixed amount small enough relative to the capacity of the digestive tract into the digestive tract (the second gas supply mode) in addition to a gas supply mode of supplying gas into the digestive tract so that the pressure inside the digestive tract becomes a set pressure (the first gas supply mode). This allows functional tests of the digestive tract such as tests for functional dyspepsia (FD) and irritable bowel syndrome (IBS) to be performed easily and in detail without increasing the workload for operators.

Also, in this description of the present invention, "small enough relative to the capacity of the digestive tract" signifies "preferably 10% or below and more preferably 5% or below with respect to the capacity of the digestive tract".

In an aspect of the gas supply apparatus according to the present invention, the capacity of the digestive tract is set or measured beforehand.

For example, the method for measuring the capacity of a digestive tract may include: supplying a fixed amount of gas in the digestive tract and estimating the capacity of the target digestive tract on the pressure change before and after the supply of gas so as to determine the capacity of the digestive tract based on the estimated capacity.

In an aspect, the gas supply apparatus according to the present invention further includes an operation device which instructs execution of the supply of gas into the digestive tract, wherein in response to an operation on the operation device, the second control device supplies the fixed amount of the gas small enough relative to the capacity of the digestive tract into the digestive tract.

According to the aspect, a fixed amount of gas is supplied to the digestive tract in response to an operation on the operation device. Thus, repeatedly performing an operation on the operation device allows pressure in the digestive tract to be easily adjusted to a target pressure without an overshoot.

Also, in the aspect, it is preferable that the operation device be an operation button arranged on a front panel in a casing of the gas supply apparatus. This allows an operator to supply a fixed amount of gas into the digestive tract by pressing the operation button.

In an aspect, the gas supply apparatus according to the present invention further includes a display device which indicates the pressure in the digestive tract according to a result detected by the pressure detecting device.

According to the aspect, the operator can feed a fixed amount of gas into the digestive tract while checking pressure in the digestive tract. This allows the operator to adjust the pressure in the digestive tract to a target pressure without inflicting pain on the patient.

In an aspect of the gas supply apparatus according to the present invention, the second control device stops the supply of the gas into the digestive tract when the pressure in the digestive tract exceeds a set pressure.

According to the aspect, the supply of gas into the digestive tract is automatically stopped when pressure in the digestive tract exceeds the set pressure in the second gas supply mode. This can prevent pain from inflicting on the patient and lighten the workload for the operator.

In an aspect, the gas supply apparatus according to the present invention further includes a setting device which sets the amount of the gas supplied into the digestive tract in the second gas supply mode.

According to the aspect, the amount of gas supplied into the digestive tract can be adjusted according to the condition or the symptom of a patient. This allows improved accuracy in diagnosis.

In an aspect, the gas supply apparatus according to the present invention further includes a pressure detection conduit for detecting a pressure in the digestive tract, the pressure detection conduit which is separately constituted from the gas supply conduit, wherein the pressure detecting device detects the pressure in the digestive tract through the pressure detection conduit.

According to the aspect, the pressure detection conduit for detecting a pressure in the digestive tract is separately constituted from the gas supply conduit for supplying gas into the digestive tract. This enables the detection of pressure in the digestive tract with stability and reliability without being affected by the supply of gas.

In an aspect of the gas supply apparatus according to the present invention, at least a part of the gas supply conduit is a conduit which is provided to an insertion part of an endoscope, an insertion aid for guiding the insertion part into a body cavity or an external instrument disposed along the insertion part.

This aspect describes a specific aspect of the present invention in which at least a part of the gas supply conduit is constituted with an insertion part of an endoscope, an insertion aid for guiding the insertion part into a body cavity or an external instrument disposed along the insertion part. This means that an apparatus of a simple configuration without any special tool can supply gas into the digestive tract.

In an aspect of the gas supply apparatus according to the present invention, the second gas supply mode is a gas supply mode of diagnostic testing for functional dyspepsia or irritable bowel syndrome.

When diagnostic testing for functional dyspepsia or irritable bowel syndrome is performed as in the case of the aspect, the effect of the present invention is significant.

According to the present invention, a gas supply apparatus includes a gas supply mode of supplying a fixed amount of gas small enough relative to the capacity of a digestive tract into the digestive tract (the second gas supply mode) in addition to a gas supply mode of supplying gas into the digestive tract so that a pressure inside the digestive tract becomes a set pressure (the first gas supply mode). This allows functional tests of the digestive tract such as tests for functional dyspepsia (FD) and irritable bowel syndrome (IBS) to be performed easily and in detail without increasing the workload for operators.

DETAILED DESCRIPTION OF THE PREFERRED EMBODIMENTS

Preferred embodiments in accordance with the present invention will now be described in detail with reference to the appended drawings.

The inventors have extensively studied and newly found that, by applying a gas supply apparatus for supplying carbon dioxide into the digestive tract to a functional test of the digestive tract, an inside of the digestive tract can be adjusted to a certain low pressure state with a simple device configuration without inflicting pain on the patient and a digestive tract sensation can be quantitatively evaluated.

Figure 1:
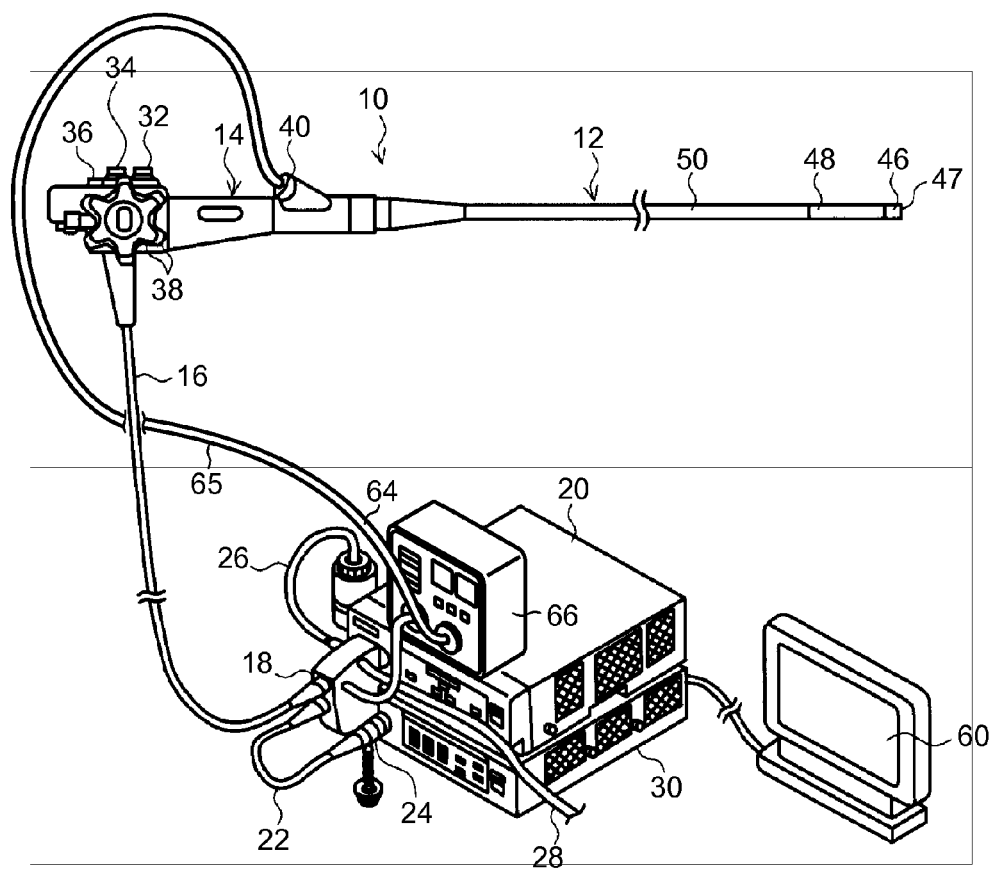
FIG. 1 is an overall configuration diagram illustrating a configuration outline of an endoscope system including a gas supply apparatus in accordance with an embodiment of the present invention.

FIG. 1 is an overall configuration diagram illustrating a configuration outline of an endoscope system including a gas supply apparatus in accordance with an embodiment of the present invention. With reference to FIG. 1, the endoscope system mainly includes an endoscope 10, a light source device 20, a processor 30, and a gas supply apparatus 66.

The endoscope 10 includes an insertion part 12 that is inserted into the digestive tract (e.g. stomach and the large intestine) of a patient and a hand operation section 14 connected to the insertion part 12. A universal cable 16 is connected to the hand operation section 14. An LG (light guide) connector 18 is provided at one end of the universal cable 16. The LG connector 18 is detachably connected to the light source device 20 so that illumination light can be transmitted to illumination optical systems 54 (refer to FIG. 2) described later. Also, an electrical connector 24 is connected to the LG connector 18 via a cable 22. The electrical connector 24 is detachably connected to the processor 30. Also, a gas/water supply tube 26 and an aspiration tube 28 are connected to the LG connector 18.

The hand operation section 14 has a gas/water supply button 32, an aspiration button 34, a shutter button 36, and a function switching button (operation button) 37 provided on it side by side. The hand operation section 14 further includes a pair of angle knobs 38, 38 and a forceps insertion opening 40.

The insertion part 12, on the other hand, includes a distal end portion 46, a bending portion 48 and a flexible portion 50. The bending portion 48 is remotely bent/operated by rotating the pair of angle knobs 38, 38 provided on the hand operation section 14. This allows a distal end surface 47 of the distal end portion 46 to be oriented in a desired direction.

Figure 2:
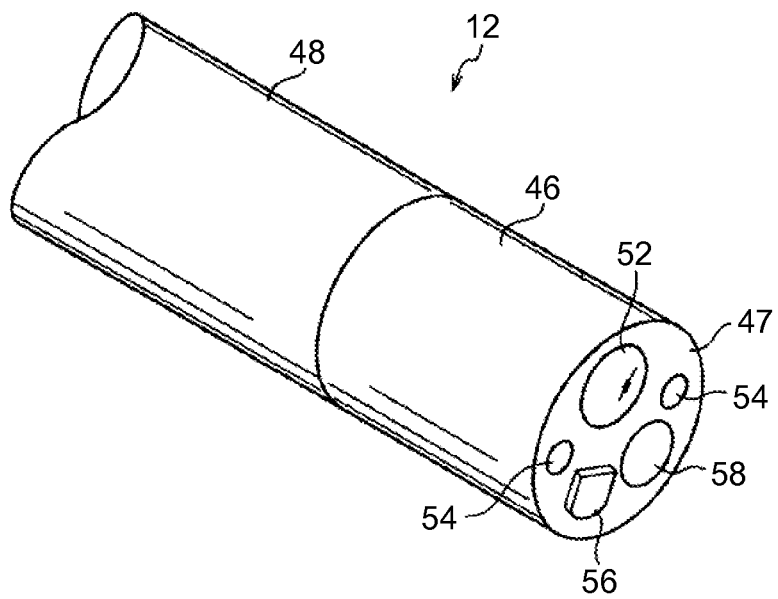
FIG. 2 is a perspective view of an end of an insertion part of the endoscope.

With reference to FIG. 2, the distal end surface 47 of the distal end portion 46 is provided with an observation optical system 52, the illumination optical systems 54, 54, a gas/water supply nozzle 56 and a forceps port 58. At the rear of the observation optical system 52, a charge-coupled device (CCD, not shown) is disposed. A signal cable is connected to a substrate that supports the CCD. The signal cable is inserted into the insertion part 12, the hand operation section 14 and the universal cable 16 of FIG. 1, extended up to the electrical connector 24, and connected to the processor 30. Thus, an image captured by the observation optical system 52 of FIG. 2 is formed on a photosensitive surface of the CCD and converted into an electric signal. Then, the electric signal is output to the processor 30 of FIG. 1 via the signal cable and converted into a video signal. This causes an observed image to be displayed on a monitor 60 connected to the processor 30.

At the rears of the illumination optical systems 54, 54 of FIG. 2, the outgoing ends of light guides (not shown) are disposed. The light guides are inserted into the insertion part 12, the hand operation section 14 and the universal cable 16 of FIG. 1. Then, the incident ends of the light guides are disposed on a light guide rod 19 (refer to FIG. 3) of the LG connector 18. Thus, when the light guide rod 19 of the LG connector 18 is connected to the light source device 20, illumination light emitted from the light source device 20 is transmitted to the illumination optical systems 54, 54 via the light guides, and emitted from the illumination optical systems 54, 54.

Figure 3:
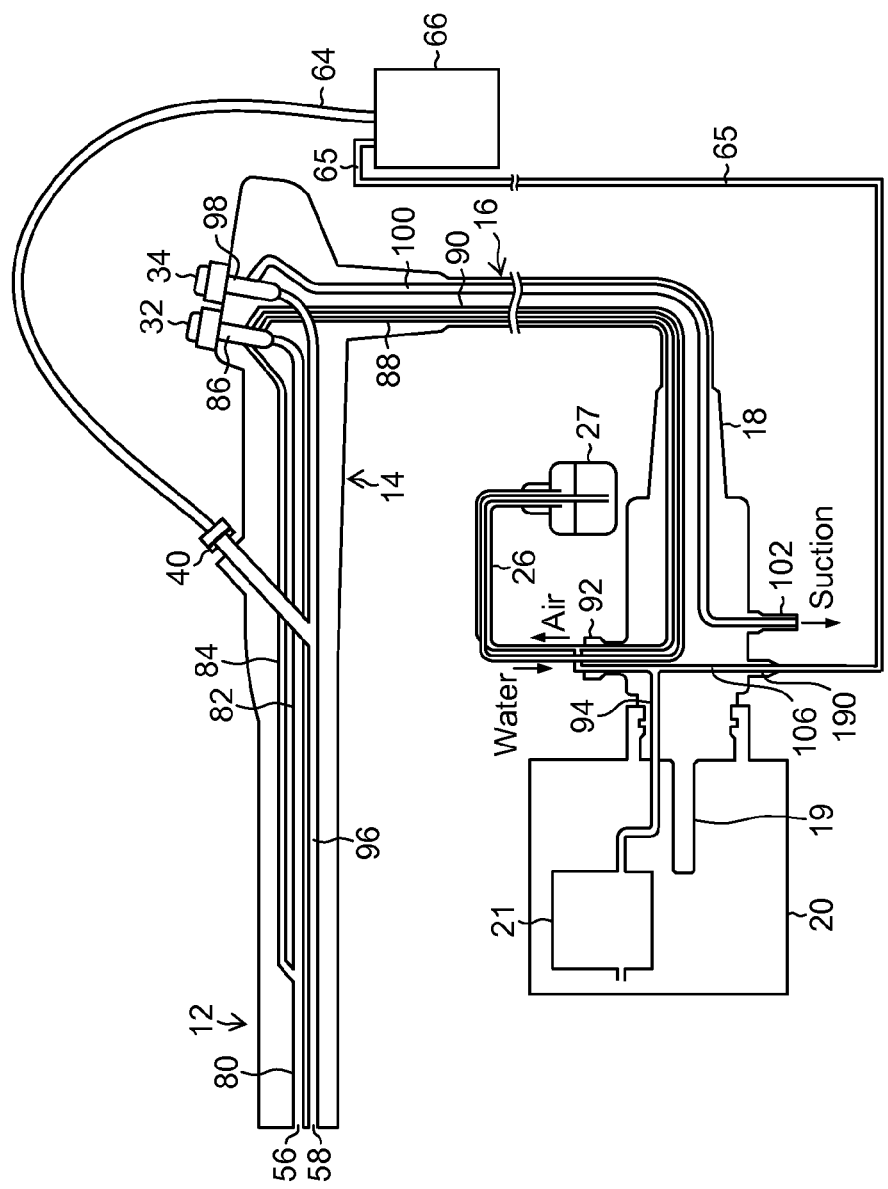
FIG. 3 is a configuration diagram schematically illustrating a conduit configuration of the endoscope.

FIG. 3 is a configuration diagram which schematically illustrates a conduit configuration of the endoscope 10. With reference to FIG. 3, a gas/water supply tube 80 is connected to the gas/water supply nozzle 56. The gas/water supply tube 80 branches into a gas supply tube 82 and a water supply tube 84, and each of them is connected to a valve 86 disposed on the hand operation section 14. An air feeding tube 88 and a water feeding tube 90 are connected to the valve 86. The gas/water supply button 32 is attached to the valve 86. When the gas/water supply button 32 is not pressed down, the gas supply tube 82 communicates with the air feeding tube 88. When the gas/water supply button 32 is pressed down, the water supply tube 84 communicates with the water feeding tube 90. The gas/water supply button 32 has an air vent (not shown), and the air feeding tube 88 communicates with the outside air via an air vent.

The air feeding tube 88 and the water feeding tube 90 are inserted into the universal cable 16, and extended up to a water supply connector 92 of the LG connector 18. The tube 26 is detachably connected to the water supply connector 92, and the end of the tube 26 is connected to a water tank 27. Then, the water feeding tube 90 communicates with below the liquid surface in the water tank 27, and the air feeding tube 88 communicates with above the liquid surface.

An air tube 94 is connected to the water supply connector 92, and the air tube 94 communicates with the air feeding tube 88. Also, when the LG connector 18 is connected to the light source device 20, the air tube 94 communicates with an air pump 21 in the light source device 20. Thus, when the air pump 21 is driven, air is fed to the air feeding tube 88 via the air tube 94. When the gas/water supply button 32 is not pressed, the air escapes to the outside via the air vent (not shown). Then, when an operator stops up the air vent, the air in the air feeding tube 88 is fed to the gas supply tube 82 and the air is injected from the gas/water supply nozzle 56. Also, when the gas/water supply button 32 is pressed down, the air feeding tube 88 and the gas supply tube 82 are isolated. Consequently, air supplied to the air tube 94 is supplied to above the liquid surface in the water tank 27. This increases internal pressure in the water tank 27 so that water is fed to the water feeding tube 90. Then, water fed through the water supply tube 84 is injected from the gas/water supply nozzle 56. Water or air is injected from the gas/water supply nozzle 56 in this way and sprayed on the observation optical system 52 so that the observation optical system 52 is cleaned.

On the other hand, a forceps tube 96 is connected to the forceps port 58. The forceps tube 96 branches into and communicates with the forceps insertion opening 40 and a valve 98. Thus, inserting a treatment tool such as a forceps from the forceps insertion opening 40 allows the treatment tool to be guided out of the forceps port 58. An aspiration tube 100 is connected to the valve 98. The aspiration button 34 is attached to the valve 98. When the aspiration button 34 is not pressed down, the aspiration tube 100 communicates with the outside air. When the aspiration button 34 is pressed down, the aspiration tube 100 is connected to the forceps tube 96. The aspiration tube 100 is extended up to an aspiration connector 102 of the LG connector 18. Connecting the tube 28 (refer to FIG. 1) to the aspiration connector 102 causes the aspiration tube 100 to communicate with an aspirator (not shown). Thus, pressing the aspiration button 34 with the aspirator driven permits a lesion or the like to be aspirated through the forceps port 58.

One end of an automatic gas supply tube 64 is detachably connected to the forceps insertion opening 40, and the other end of the automatic gas supply tube 64 is connected to an automatic gas supply connector 144 (refer to FIG. 4) in the gas supply apparatus 66. This allows carbon dioxide fed from the automatic gas supply connector 144 of the gas supply apparatus 66 to go through the automatic gas supply tube 64, the forceps insertion opening 40 and the forceps tube 96 and to be injected out of the forceps port 58.

A gas connector 190 is also provided on the LG connector 18. One end of a manual gas supply tube 65 is detachably connected to the gas connector 190, and the other end of the manual gas supply tube 65 is connected to a manual gas supply connector 145 (refer to FIG. 4) in the gas supply apparatus 66. Inside the LG connector 18, one end of a gas tube 106 is connected to the gas connector 190, and the other end of the gas tube 106 communicates with the air feeding tube 88 via the air tube 94. This allows carbon dioxide fed from the manual gas supply connector 145 of the gas supply apparatus 66 to be supplied to the air feeding tube 88 via the manual gas supply tube 65, the gas connector 190, the gas tube 106 and the air tube 94. Then, in like manner with air being supplied from the air pump 21 of the light source device 20 to the air feeding tube 88, water or carbon dioxide is injected through the gas/water supply nozzle 56 when an operator operates the gas/water supply button 32.

Also, it is preferable that in order not to supply carbon dioxide fed from the gas supply apparatus 66 and air fed from the air pump 21 simultaneously to the air feeding tube 88, a control means (not shown) which alternatingly controls the driving of these apparatuses be provided. For example, the control means may be provided on the light source device 20, the gas supply apparatus 66 or the processor 30 to exercise control so that the supply of carbon dioxide fed from the gas supply apparatus 66 takes preference (priority) over the supply of air fed from the air pump 21. In this case, the air pump 21 is used as a backup gas supply source in preparation for gas running out of a carbon dioxide cylinder 110.

As described in detail later, the gas supply apparatus 66 according to the embodiment includes a gas supply mode for endoscopy (a first gas supply mode) and a gas supply mode for FD/IBS diagnoses (a second gas supply mode) as gas supply modes for supplying carbon dioxide into the digestive tract. The gas supply mode for endoscopy is suitable for ensuring the vision of the endoscope and the operation area of the treatment tool. The mode is designed to supply carbon dioxide into a digestive tract so that a pressure inside the digestive tract becomes a set pressure according to the result detected by pressure detecting means which detects the pressure inside the digestive tract. The gas supply mode for FD/IBS diagnoses is suitable for diagnostic tests for functional dyspepsia (FD) and irritable bowel syndrome (IBS). The mode is designed to supply a fixed amount of carbon dioxide into a digestive tract, and the amount is sufficiently small relative to the capacity of the digestive tract.

Figure 4:
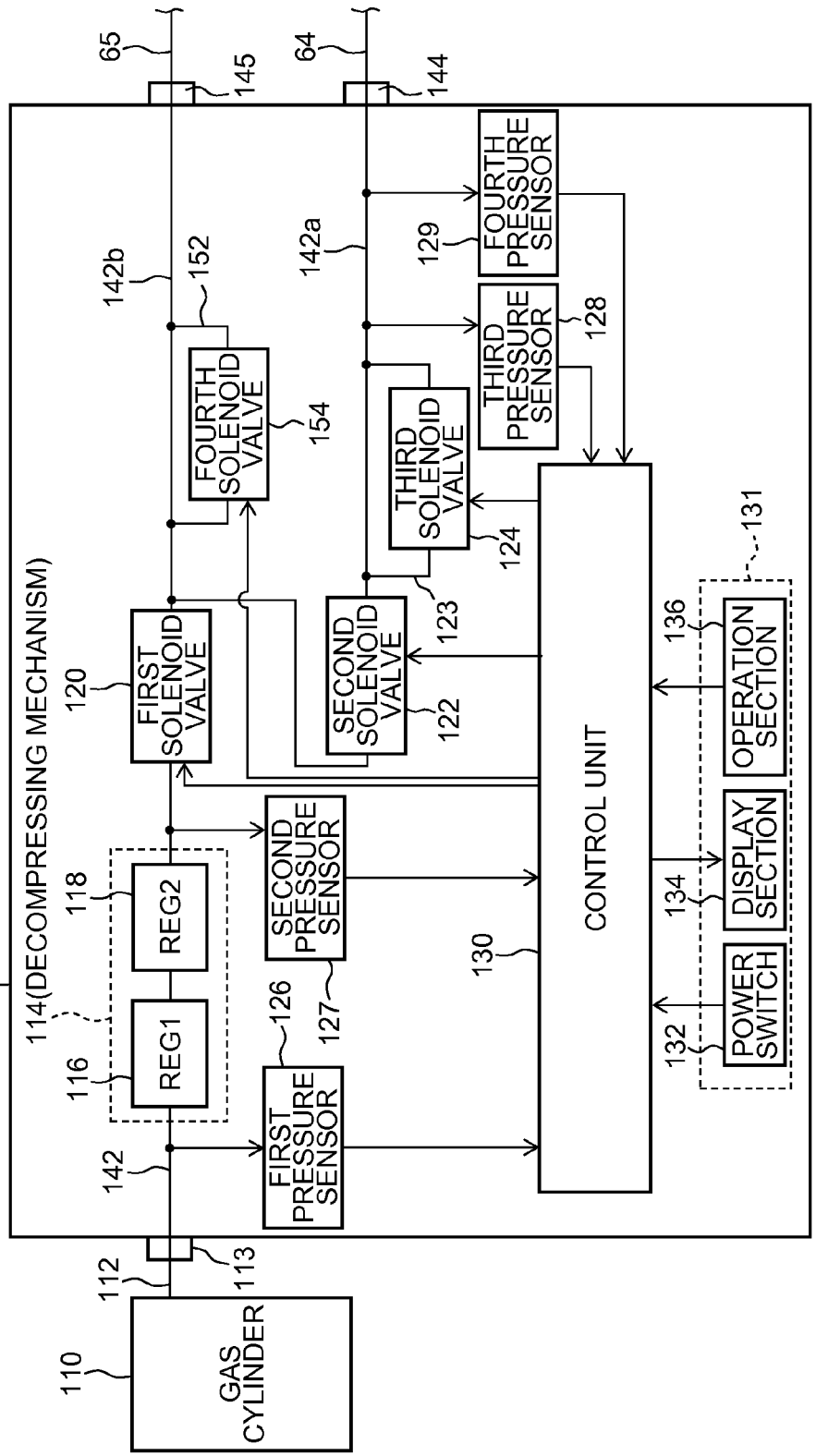
FIG. 4 is a block diagram illustrating a configuration of the gas supply apparatus.

FIG. 4 is a block diagram illustrating a configuration of the gas supply apparatus 66. With reference to FIG. 4, the gas supply apparatus 66 includes a decompressing mechanism 114, first to fourth solenoid valves 120, 122, 124, 154, first to fourth pressure sensors 126, 127, 128, 129, a control unit 130, and a front panel (operation panel) 131.

One end of a high-pressure hose 112 is detachably connected to a high-pressure connector 113 of the gas supply apparatus 66 and the other end is connected to the carbon dioxide cylinder 110 which is a gas supply source. In other words, the gas supply apparatus 66 communicates with the carbon dioxide cylinder 110 via the high-pressure hose 112. Thus, the carbon dioxide from the carbon dioxide cylinder 110 is supplied to the high-pressure connector 113 via the high-pressure hose 112.

One end of an internal conduit 142 provided inside the gas supply apparatus 66 is connected to the high-pressure connector 113. The decompressing mechanism 114 is arranged to the internal conduit 142 in order to decompress carbon dioxide fed from the carbon dioxide cylinder 110 to a set pressure. The internal conduit 142 branches into two conduits 142a, 142b (hereinafter referred to as a first branch conduit 142a and a second branch conduit 142b) at the outlet side (opposite to the high-pressure connector 113) of the decompressing mechanism 114.

The decompressing mechanism 114 is decompression means which gradually (in stages) decompresses carbon dioxide fed from the carbon dioxide cylinder 110 to a proper pressure and is composed of two regulators (reducing valves) 116, 118 which are arranged in series. For example, the first regulator 116 decompresses carbon dioxide fed from the carbon dioxide cylinder 110 from 10 MPa to 0.3 MPa. Then, the second regulator 118 decompresses the carbon dioxide decompressed with the first regulator 116 from 0.3 MPa to 0.05 MPa.

The first pressure sensor 126 is pressure detecting means which detects pressure of carbon dioxide fed from the carbon dioxide cylinder 110 and is connected to the internal conduit 142 between the high-pressure connector 113 and the decompressing mechanism 114. Results detected by the first pressure sensor 126 are output to the control unit 130.

The second pressure sensor 127 is pressure detecting means which detects pressure of carbon dioxide decompressed by the decompressing mechanism 114 and is connected to the internal conduit 142 between the decompressing mechanism 114 and the first solenoid valve 120. Results detected by the second pressure sensor 127 are output to the control unit 130.

The first solenoid valve 120 is an opening and closing means capable of having the internal conduit 142 communicated or interrupted. The valve 120 is provided at a place on the internal conduit 142, which is located downstream of the decompressing mechanism 114 and upstream of a point where the internal conduit 142 divides into each of the branch conduits 142a and 142b. The first solenoid valve 120 opens or closes according to a control signal output from the control unit 130. The open/close mechanism of the first solenoid valve 120 causes the internal conduit 142 to be communicated or interrupted so that the supply/non-supply of carbon dioxide to each of the branch conduits 142a, 142b is performed in a collective manner.

The first branch conduit 142a is a conduit for automatically supplying carbon dioxide into a digestive tract and the end of the conduit 142a is connected to the automatic gas supply connector 144. The second solenoid valve 122 is provided on the first branch conduit 142a in the upstream direction (the branch point side of the internal conduit 142). The second solenoid valve 122, an opening and closing means capable of having the first branch conduit 142a communicated or interrupted, opens or closes according to a control signal output from the control unit 130.

A bypass conduit 123 that detours a portion (throttle portion) of the first branch conduit 142a is connected to downstream of the second solenoid valve 122 on the first branch conduit 142a. The third solenoid valve 124 is disposed at some midpoint in the bypass conduit 123 and acts as flow regulating means which regulates a flow rate of carbon dioxide supplied automatically into a digestive tract via the automatic gas supply tube 64. The third solenoid valve 124 is opening and closing means which is capable of having the bypass conduit 123 communicated or interrupted, opens or closes according to a control signal output from the control unit 130.

Also, it is preferable that the third solenoid valve 124 be composed of a flow regulating valve (solenoid proportional valve) capable of steplessly controlling the flow rate in proportion to the control signal (current value). This enables the flow rate of carbon dioxide supplied automatically into the digestive tract via the automatic gas supply tube 64 to be controlled with high accuracy.

The third, fourth pressure sensors 128, 129 are pressure detecting means which detect pressure in a digestive tract via a gas supply conduit (the first branch conduit 142a, the automatic gas supply tube 64, and the forceps tube 96) for supplying carbon dioxide into the digestive tract. Each of the pressure sensors 128, 129 is connected to the first branch conduit 142a at a position located downstream of the downstream side connecting position of the bypass conduit 123. Results detected by each of the pressure sensors 128, 129 are output to the control unit 130.

In the embodiment, either one of the third pressure sensor 128 and the fourth pressure sensor 129 is used as a main sensor while the other pressure sensor is used as a backup sensor. This enables the detection of pressure in the digestive tract with the backup sensor in the event of a failure in the main sensor, leading to improved reliability in the detection of pressure in the digestive tract.

The second branch conduit 142b is a conduit for manually supplying carbon dioxide into a digestive tract and the end of the conduit 142b is connected to the manual gas supply connector 145. A bypass conduit 152 that detours a portion (throttle portion) of the second branch conduit 142b is connected to places on the second branch conduit 142b. The fourth solenoid valve 154 is disposed at some midpoint in the bypass conduit 152 and acts as flow regulating means which regulates the flow rate of carbon dioxide supplied into a digestive tract via the manual gas supply tube 65. The fourth solenoid valve 154 is opening and closing means which is capable of having the bypass conduit 152 communicated or interrupted, and opens or closes according to a control signal output from the control unit 130.

The front panel (operation panel) 131 is arranged on the front of a casing, a component of the gas supply apparatus 66. The front panel 131 includes a power switch 132, a display section 134, and an operation section 136, and each of these components is connected to the control unit 130.

Figure 5:
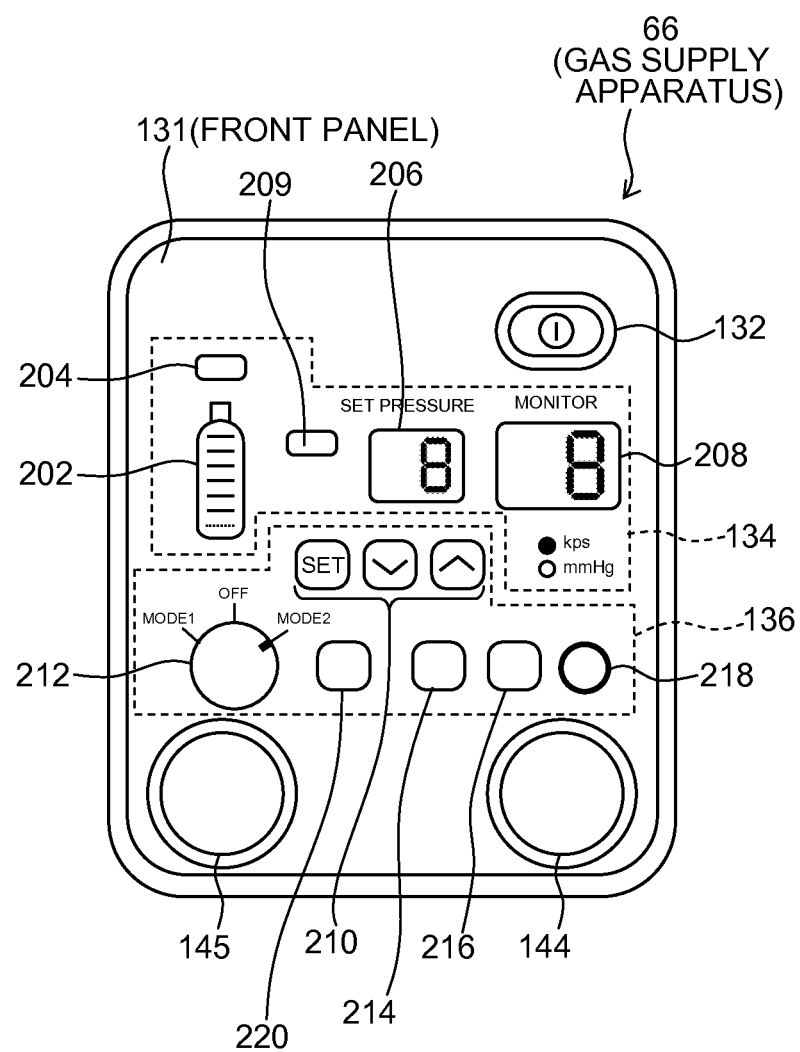
FIG. 5 illustrates a front panel of the gas supply apparatus.

FIG. 5 illustrates the front panel 131 of the gas supply apparatus 66. With reference to FIG. 5, the display section 134 includes: a remaining amount indicator 202 for indicating the amount of remaining carbon dioxide in the carbon dioxide cylinder 110; a gas warning indicator 204 for indicating a warning when the amount of remaining carbon dioxide has dropped to a predetermined level or below; a set pressure display 206 for displaying a set pressure in a digestive tract; a pressure display 208 for displaying a pressure (present pressure) in the digestive tract; and a pressure warning indicator 209 for indicating a warning when the pressure inside the digestive tract exceeds the set pressure.

The operation section 136 includes: a pressure setting unit 210 for setting a set pressure in a digestive tract; a gas supply mode selecting unit 212 for selecting a gas supply mode; a gas supply button (fixed-amount-gas supply button) 214 which acts as operation means for instructing execution of the supply of a fixed amount of gas into the digestive tract in the gas supply mode for FD/IBS diagnoses; a capacity estimation button 216 for instructing the supply of a fixed amount of carbon dioxide (e.g. about 5 ml) into the digestive tract so as to estimate the capacity of the digestive tract in the gas supply mode for FD/IBS diagnoses; a gas-flow rate setting knob 218 which acts as setting means which sets the air supply amount (volume) of carbon dioxide supplied into the digestive tract in the gas supply mode for FD/IBS diagnoses; and a gas supply mode end button 220 for instructing the end of the gas supply mode. An operation signal corresponding to an operation done with each part of the operation section 136 is sent to the control unit 130.

With reference back to FIG. 4, the control unit 130 includes a CPU and a memory (both not shown) or the like, and controls the overall operation of the gas supply apparatus 66. The memory stores control programs and various kinds of setting information (e.g. a set pressure, a flow rate and so on in the digestive tract set by the pressure setting unit 210) for operating the gas supply apparatus 66.

The control unit 130 has the remaining amount indicator 202 indicate the amount of remaining carbon dioxide in the carbon dioxide cylinder 110 according to the result detected by the first pressure sensor 126. Also, the control unit 130 causes the gas warning indicator 204 to indicate a warning when the amount of remaining carbon dioxide has dropped to a predetermined level or below and issues an alarm. This enables the carbon dioxide cylinder 110 to be replaced with a new cylinder before remaining carbon dioxide runs out.

Also, according to a result detected by the third pressure sensor 128 or the fourth pressure sensor 129 as pressure detecting means, the control unit 130 indicates the pressure in the digestive tract on the pressure display 208 and the set pressure in the digestive tract set by the pressure setting unit 210 on the set pressure display 206.

In the embodiment, the control unit 130 acts as mode switching means which switches the gas supply apparatus 66 to a gas supply mode selected by the gas supply mode selecting unit 212 including a change-over switch, and acts as first or second control means which exercises control according to the selected gas supply mode.

Figure 6:
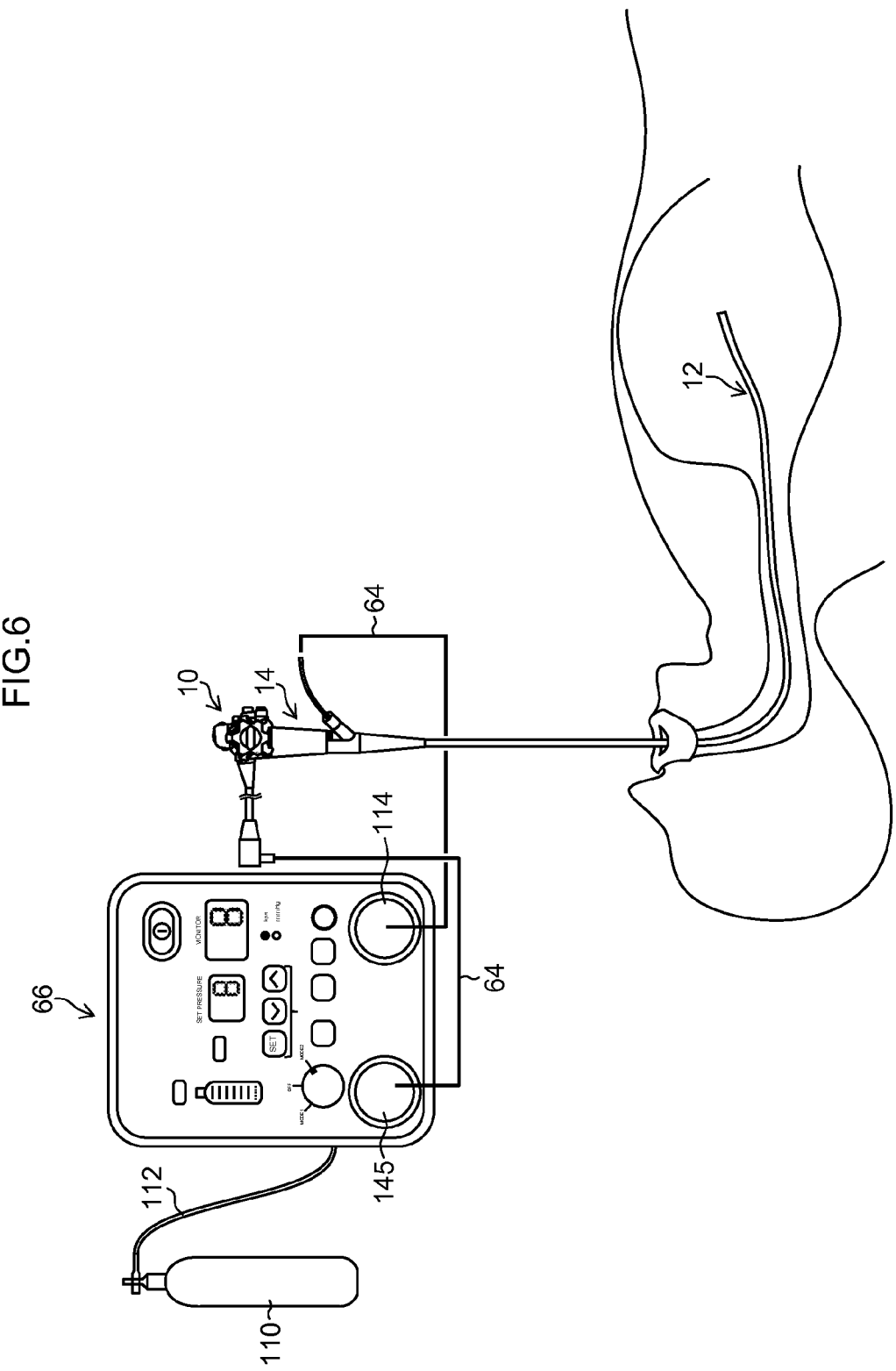
FIG. 6 illustrates a use state of the endoscope system according to the embodiment is used.

With reference to FIG. 6, for example, an endoscope system configured according to the embodiment described above supplies carbon dioxide into a digestive tract via the internal conduit of the endoscope 10 from the gas supply apparatus 66 in a state where the insertion part 12 of the endoscope 10 is inserted into the digestive tract of a patient. Note that examples of the digestive tract which the insertion part 12 of the endoscope 10 is inserted into include a stomach, a gullet, a small intestine (a duodenum, a jejunum, an ileum) and a large intestine (a cecum, a colon, a rectum). It is particularly preferable that the digestive tract be a stomach, a large intestine or the like. FIG. 6 illustrates a state where the insertion part 12 of the endoscope 10 is inserted into the stomach via the gullet from the mouth of the patient.

Figure 7:
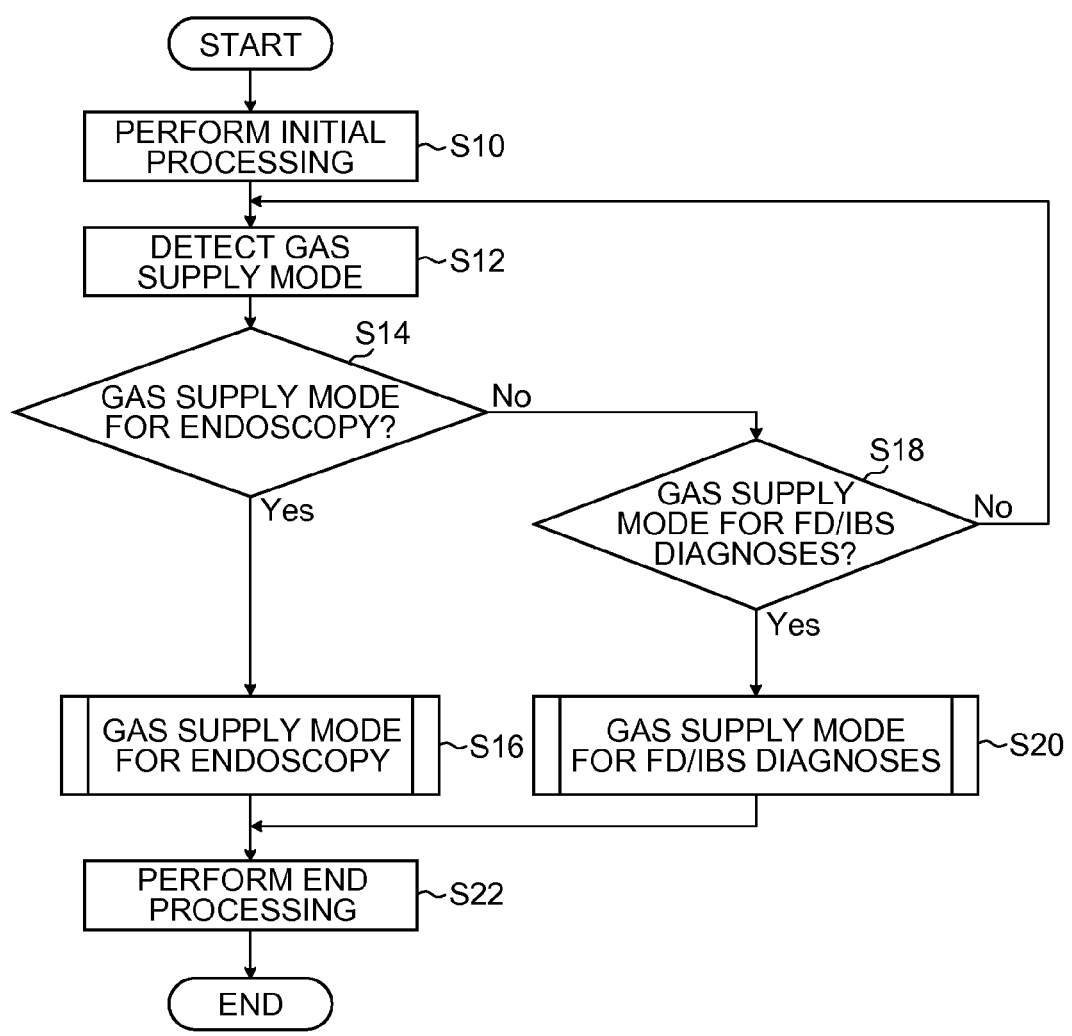
FIG. 7 is a flowchart showing an example of the operation of the gas supply apparatus.
Figure 8:
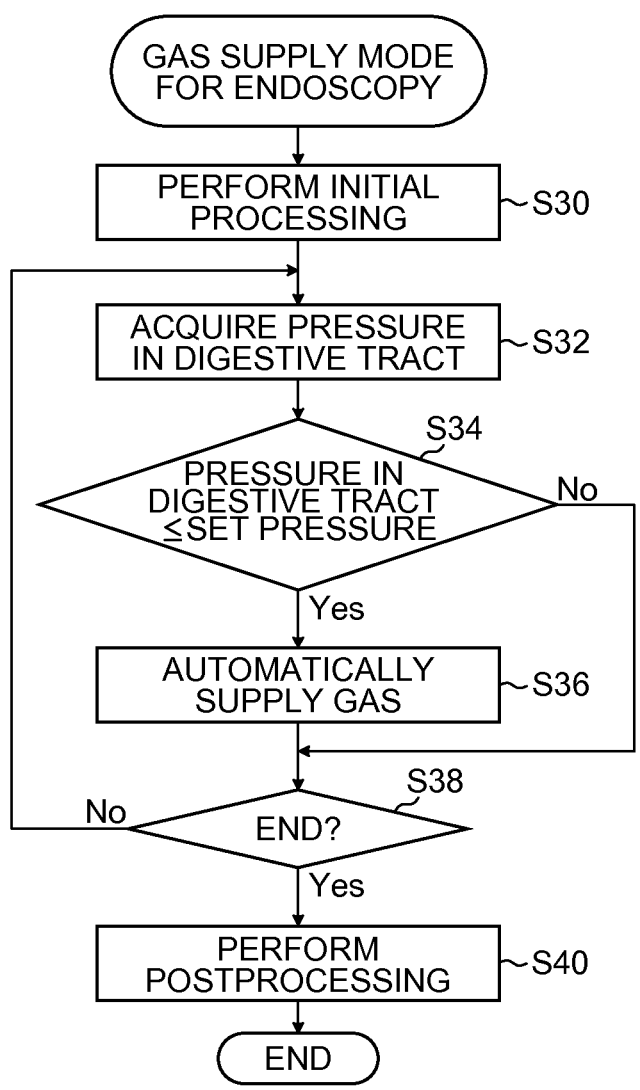
FIG. 8 is a flowchart showing an example of a process performed in a gas supply mode for endoscopy.
Figure 9:
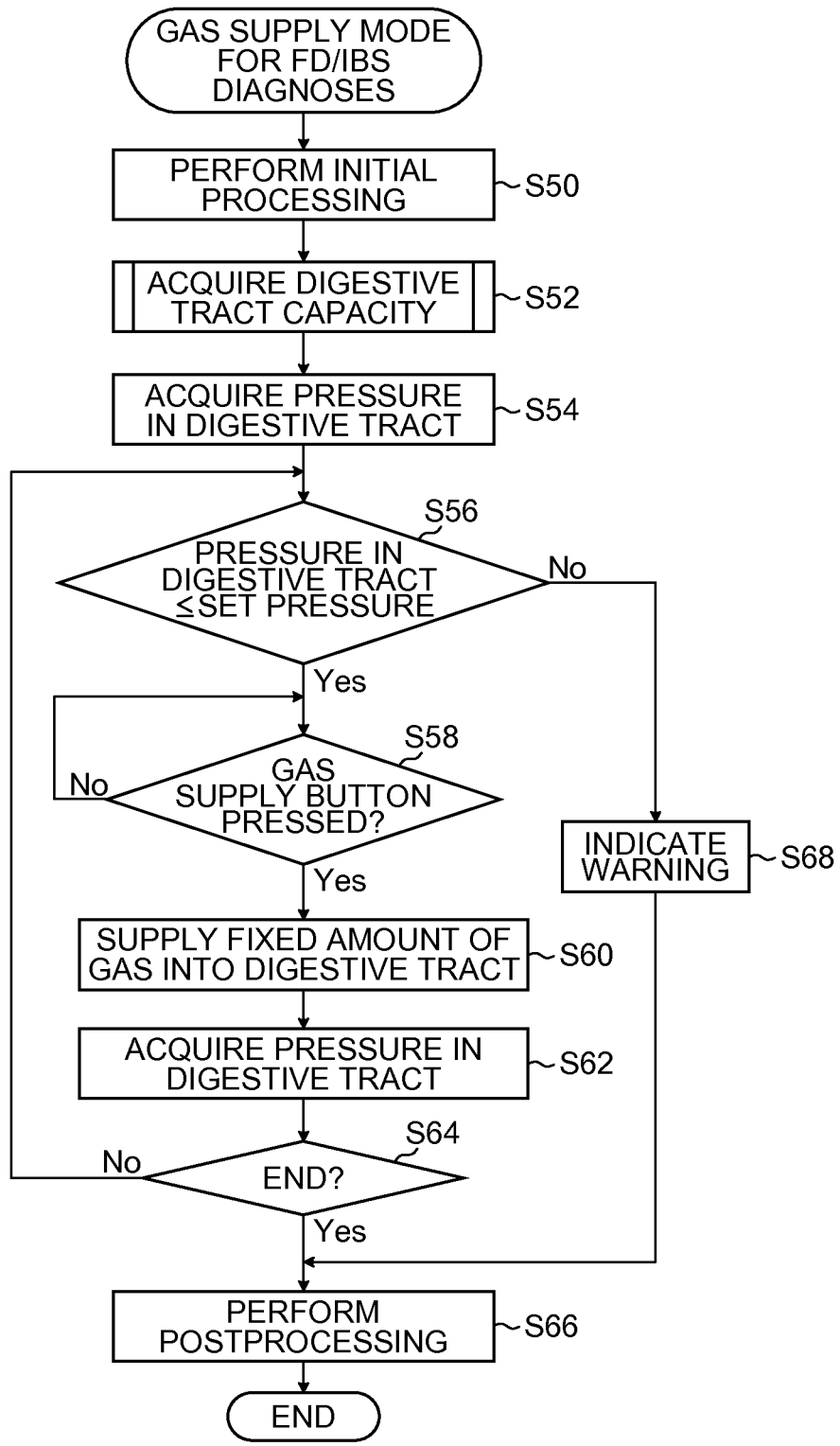
FIG. 9 is a flowchart showing an example of a process performed in a gas supply mode for FD/IBS diagnoses.

With reference to FIGS. 7 to 9, the operation of the gas supply apparatus 66 according to the embodiment will now be described.

FIG. 7 is a flowchart showing an example of the operation of the gas supply apparatus 66.

First of all, when the gas supply apparatus 66 is turned on with the power switch 132, initial processing such as operational checks on each part is performed (step S10).

Then the control unit 130 detects the gas supply mode selected by the gas supply mode selecting unit 212 composed of a change-over switch (step S12). An operation of the change-over switch is performed by an operator.

Then, the control unit 130 acts as the gas supply mode switching means and switches the gas supply apparatus 66 into the gas supply mode selected by the change-over switch of the gas supply mode selecting unit 212.

Specifically, first of all, the control unit 130 determines whether or not the gas supply mode selecting unit 212 selects the gas supply mode for endoscopy (step S14). When the gas supply mode for endoscopy is selected, the control unit 130 acts as the "first control means" in the present invention so as to exercise control according to the gas supply mode for endoscopy (step S16). On the other hand, when the gas supply mode for endoscopy is not selected, the process proceeds to step S18.

Then, the control unit 130 determines whether or not the gas supply mode for FD/IBS diagnoses is selected (step S18). When the gas supply mode for FD/IBS diagnoses is selected, the control unit 130 acts as the "second control means" in the present invention so as to exercise control according to the gas supply mode for FD/IBS diagnoses (step S20). On the other hand, when the gas supply mode for FD/IBS diagnoses is not selected, the process returns to the step S12 to perform the same processing.

After processing at the step S16 or the step S20 is performed, a predetermined end processing is performed (step S22).

With reference to FIG. 8, the gas supply mode for endoscopy will now be described. FIG. 8 is a flowchart showing an example of a process performed in the gas supply mode for endoscopy.

First of all, as a preprocessing, the control unit 130 causes the first solenoid valve 120 to be in an open state and makes the internal conduit 142 communicated (step S30). This makes the gas supply apparatus 66 ready for manually supplying carbon dioxide into the digestive tract in response to the operation of the gas/water supply button 32 on the endoscope 10.

Then, the control unit 130 acquires (obtains) a pressure in the digestive tract (step S32). The detection of the pressure in the digestive tract is performed by the third pressure sensor 128 or the fourth pressure sensor 129 acting as the pressure detecting means. The detected result is output to the control unit 130. The control unit 130 corrects a loss in pressure which occurs in travel between the pressure detection position and the inside of the digestive tract so as to calculate a real pressure in the digestive tract.

Then, the control unit 130 determines whether or not the pressure in the digestive tract is smaller than or equal to the set pressure (threshold) (step S34).

When the pressure in the digestive tract is smaller than or equal to the set pressure, the control unit 130 causes the second solenoid valve 122 to be in an open state and makes the first branch conduit 142a communicated so as to automatically supply carbon dioxide into the digestive tract (step S36). Then, the process proceeds to the next step S38. On the other hand, when the pressure in the digestive tract exceeds the set pressure, the process skips the step S36 to step S38.

Then, the control unit 130 determines whether or not the gas supply mode end button 220 has been pressed (step S38). When the gas supply mode end button 220 has not been pressed, the process returns to the step S32 to perform the same processing.

On the other hand, when the gas supply mode end button 220 has been pressed, the control unit 130 performs a postprocessing, that is, causing the first solenoid valve 120 to be in a close state (step S40). This causes the internal conduit 142 to be interrupted, disabling the supply of carbon dioxide from each of the branch conduits 142a, 142b to the digestive tract (non-supply state).

With reference to FIG. 9, the gas supply mode for FD/IBS diagnoses will now be described. FIG. 9 is a flowchart showing an example of a process performed in the gas supply mode for FD/IBS diagnoses.

First of all, as a preprocessing, the control unit 130 causes the first solenoid valve 120 to be in an open state and makes the internal conduit 142 communicated (step S50). This makes the gas supply apparatus 66 is set in a state capable of manually supplying carbon dioxide into the digestive tract in response to the operation of the gas/water supply button 32 on the endoscope 10.

Then, the control unit 130 acquires a capacity of the digestive tract (digestive tract capacity) through a process for acquiring digestive tract capacity as describe later (step S52). A method for obtaining the digestive tract capacity may include the use of a preset or pre-measured digestive tract capacity. In this case, digestive tract capacity can be acquired by referring to a memory (not shown) of the control unit 130 which stores the preset or pre-measured digestive tract capacity.

Then, the control unit 130 acquires a pressure in the digestive tract (step S54). The detection of the pressure in the digestive tract is performed by the third pressure sensor 128 or the fourth pressure sensor 129 acting as the pressure detecting means. The detected result is output to the control unit 130. The control unit 130 corrects a loss in pressure which occurs in travel between the pressure detection position and the inside of the digestive tract and calculates a real pressure in the digestive tract. At this time, the calculated real pressure (pressure after correction) in the digestive tract calculated by the control unit 130 is displayed on the pressure display 208. Also, the set pressure in the digestive tract set by the pressure setting unit 210 is displayed on the set pressure display 206.

Then, the control unit 130 determines whether or not the pressure in the digestive tract is smaller than or equal to the set pressure (threshold) (step S56). When the pressure in the digestive tract exceeds the threshold, the control unit 130 acts as prohibiting means which prohibits the supply of carbon dioxide into the digestive tract and processing at steps S58 to S64 is skipped. A warning is indicated on the pressure warning indicator 209 of the gas supply apparatus 66 (step S68), and the process proceeds to step S66.

On the other hand, when the pressure in the digestive tract is smaller than or equal to the set pressure, the control unit 130 determines whether or not the gas supply button 214 has been pressed (step S58). At this time, the control unit 130 enters a wait state until the gas supply button 214 is pressed, and goes to the next step S60 when the gas supply button 214 is pressed.

When the gas supply button 214 is pressed, the control unit 130 causes each of the second solenoid valve 122 and the third solenoid valve 124 to be in an open state for each set period of time so as to supply a fixed amount of carbon dioxide into the digestive tract via the automatic gas supply tube 64 (step S60). At this time, it is preferable that the amount (volume) of carbon dioxide supplied to the digestive tract be 10% or below (more preferably 5% or below) with respect to the digestive tract capacity acquired in the step S52. Setting the amount of supplied carbon dioxide in this way leads to only a 10% increase at most in pressure in the digestive tract during the supply of a fixed amount of gas (for example, when the pressure in the digestive tract is 10 mmHg, it increases only 1 mmHg at most). This enables pressure in the body cavity to be increased gradually (in stages) while the digestive tract is kept at a certain low pressure. Thus, the digestive tract sensation can be quantitatively evaluated.

Then, the control unit 130 acquires a pressure in the digestive tract in like manner with the step S54 described above (step S62). At this time, it is preferable that the third pressure sensor 128 or the fourth pressure sensor 129 as the pressure detecting means detect the pressure in the digestive tract after a predetermined period of time has elapsed since the completion of gas supply in the step S60. In the embodiment, one conduit is shared both for detecting pressure in the digestive tract and for supplying carbon dioxide into the digestive tract. Thus, both gas supply and pressure measurement can be performed in one same conduit without being affected by a time-varying pressure owing to gas supply by waiting a predetermined period of time (several tens of milliseconds to several hundreds of milliseconds) until pressure both in the digestive tract and at the pressure detection position in the gas supply apparatus 66 has been balanced after the completion of supply of a fixed amount of carbon dioxide into the digestive tract, and then performing pressure detection with the pressure detecting means (the third pressure sensor 128 or the fourth pressure sensor 129) in the gas supply apparatus 66.

Then, the control unit 130 determines whether or not the gas supply mode end button 220 has been pressed (step S64). When the gas supply mode end button 220 has not been pressed, the process returns to the step S56 to perform the same processing.

On the other hand, when the gas supply mode end button 220 has been pressed, the control unit 130 performs a postprocessing, that is, causing the first solenoid valve 120 to be in a close state (step S66). This causes the internal conduit 142 to be interrupted, disabling the supply of carbon dioxide from each of the branch conduits 142a, 142b to the digestive tract (non-supply state). Then the gas supply mode for FD/IBS diagnoses ends.

Figure 10:
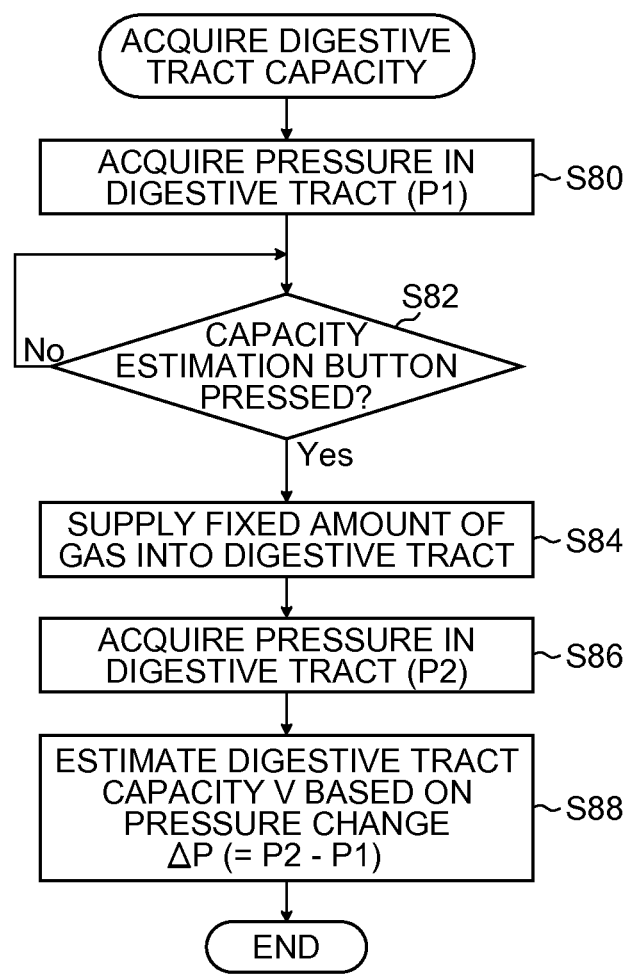
FIG. 10 is a flowchart showing an example of a process for acquiring the capacity of a digestive tract.

With reference to FIG. 10, a process for acquiring digestive tract capacity (step S52 in FIG. 9) performed in the gas supply mode for FD/IBS diagnoses will now be described. FIG. 10 is a flowchart showing an example of a process for acquiring the capacity of a digestive tract.

First of all, the control unit 130 acquires a pressure P1 (pressure before supply) in the digestive tract (step S80). The method for acquiring a pressure in the digestive tract is similar to that in the steps S54 and S62 of FIG. 9.

Then, the control unit 130 determines whether or not the capacity estimation button 216 has been pressed (step S82). At this time, the control unit 130 enters into a wait state until the capacity estimation button 216 is pressed. The process proceeds to the next step S84 when the capacity estimation button 216 is pressed.

When the capacity estimation button 216 is pressed, the control unit 130 causes each of the second solenoid valve 122 and the third solenoid valve 124 to be in an open state for each set period of time so as to supply a fixed amount of carbon dioxide into the digestive tract via the first branch conduit 142a (step S84). At this time, it is preferable that the amount (volume) of carbon dioxide supplied to the digestive tract be 5% or below (e.g. about 5 ml) with respect to the digestive tract capacity.

Then, the control unit 130 acquires a pressure P2 (pressure after supply) in the digestive tract in like manner with the step S80 (step S86). At this time, it is preferable that the detection of the pressure in the digestive tract be performed by the third pressure sensor 128 or the fourth pressure sensor 129 as the pressure detecting means after a predetermined period of time has elapsed since the completion of gas supply in the step S84. In the embodiment as described above, one same conduit is shared as both a pressure detecting conduit for detecting pressure in the digestive tract and a gas supply conduit for supplying carbon dioxide into the digestive tract. Thus, detecting pressure after a predetermined period of time enables to reduce the effect of a time-varying pressure owing to gas supply.

Then, the control unit 130 estimates a digestive tract capacity V based on a pressure change $\Delta P$ (=P2−P1) in the digestive tract before and after the supply of a fixed amount of gas (step S88). For example, the method for estimating the digestive tract capacity V includes: storing a look-up table indicating correspondences among the amount of carbon dioxide supplied into a digestive tract, the pressure change $\Delta P$ in the digestive tract and the digestive tract capacity V in a memory; and referring to the look-up table using the pressure change $\Delta P$ in the digestive tract before and after the supply of the fixed amount of carbon dioxide to determine the digestive tract capacity V.

Based on the digestive tract capacity V determined in this manner, the control unit 130 determines the amount of carbon dioxide fed into the digestive tract in the step S60 of FIG. 9. This enables the amount of gas supply to be set suitable for the patient without being affected by the difference in digestive tract capacity among individual patients as compared to an embodiment using a preset digestive tract capacity (fixed value).

As described above, the embodiment allows switching between the gas supply mode for endoscopy which offers the supply of carbon dioxide into the digestive tract so that the pressure inside the digestive tract becomes the set pressure and the gas supply mode for FD/IBS diagnoses which offers the supply of carbon dioxide in a fixed amount being small enough relative to the digestive tract capacity into the digestive tract. This permits an operator to select an optimum gas supply mode according to the use.

Particularly in the gas supply mode for FD/IBS diagnoses, a fixed amount of carbon dioxide is fed into the digestive tract every time the gas supply button 214 is pressed. Thus, repeatedly pressing the gas supply button allows pressure in the digestive tract to be easily adjusted to a target pressure without an overshoot. This also enables an operator to feed carbon dioxide into the digestive tract while checking pressure changes in the digestive tract without inflicting pain on the patient. This allows the quantitative evaluation of a digestive tract sensation by giving a constant low pressure to the digestive tract. Thus, functional tests of the digestive tract such as tests for functional dyspepsia (FD) and irritable bowel syndrome (IBS) can be performed easily and in detail.

Also, in the gas supply mode for FD/IBS diagnoses, the supply of carbon dioxide into the digestive tract is automatically prohibited when the pressure in the digestive tract exceeds the set pressure. This prevents the pressure in the digestive tract from increasing higher than a set pressure. Consequently, this can lighten the workload for operators and provide efficient diagnoses without inflicting pain on patients.

Also, setting means (the gas-flow rate setting knob 218) is provided for setting the amount of carbon dioxide supplied into the digestive tract in the gas supply mode for FD/IBS diagnoses. This enables the amount of carbon dioxide supplied into the digestive tract to be adjusted according to the condition or the symptom or the like of a patient. This allows improved accuracy in diagnosis.

Also, the embodiment has been described by taking carbon dioxide as a gas supplied into the digestive tract. The gas supplied into the digestive tract, however, is not limited to carbon dioxide. Helium gas, for example, and other gases may be used instead.

A gas supply apparatus according to the present invention has been described in detail. Application of the present invention, however, is not limited to the example described above. It should be understood that various modifications and alterations may occur insofar as they are within the scope of the present invention. Variations will now be described.

[First Variation]

Figure 11:
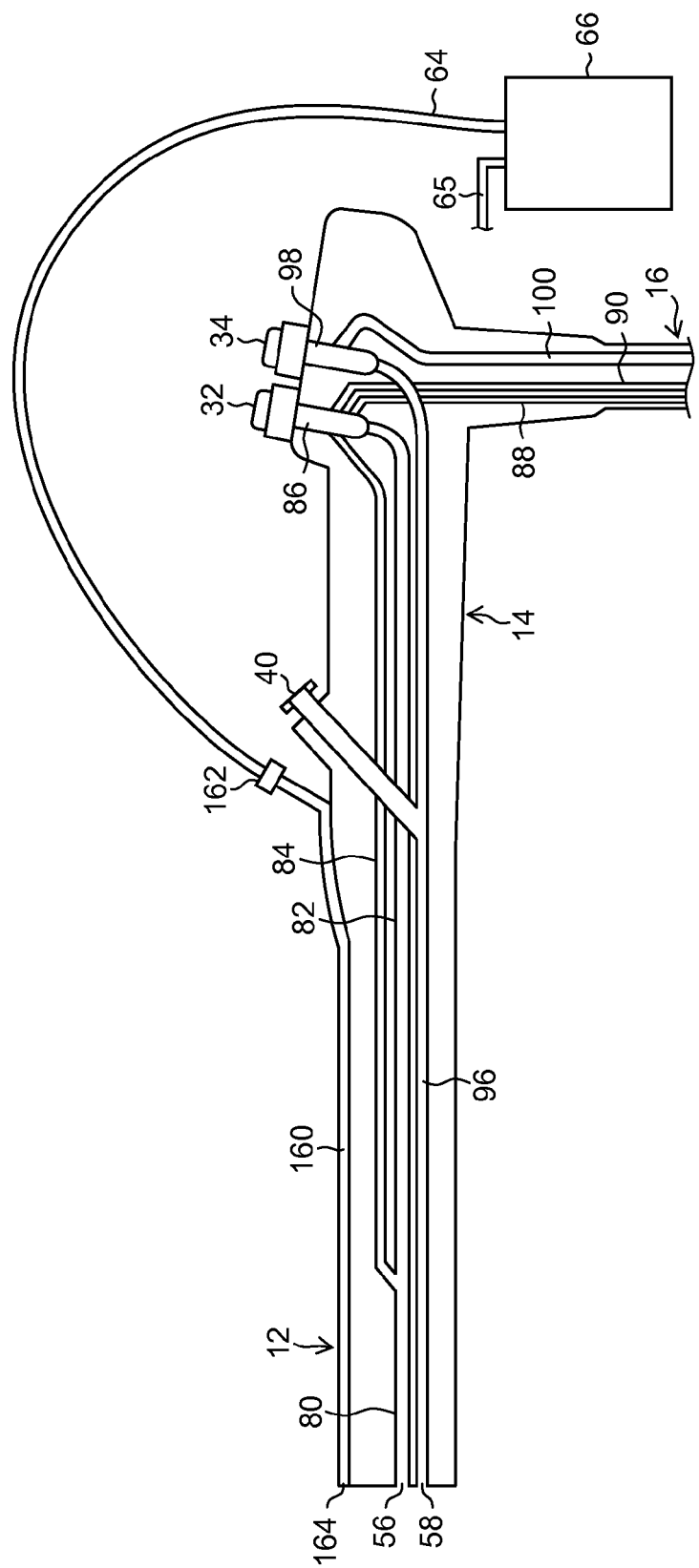
FIG. 11 is a schematic diagram illustrating a conduit configuration of the endoscope as a first variation.

FIG. 11 is a schematic diagram schematically illustrating a conduit configuration of the endoscope as a first variation. In FIG. 11, members identical or similar to those of FIG. 3 are assigned with the same reference numerals, and their descriptions are omitted.

As illustrated in FIG. 11, in the first variation, a part of a gas supply conduit for supplying carbon dioxide into a digestive tract is constituted by an external tube 160 which is an external device disposed along the longitudinal direction of an insertion part 12 of an endoscope 10. The external tube 160 is fixed to the outer circumference of the insertion part 12 of the endoscope 10 by a fixing device (not shown) such as a tape. At the proximal side of the external tube 160, a gas supply port 162 is formed. One end of an automatic gas supply tube 64 is detachably connected to the gas supply port 162. The gas supply port 162 communicates with a distal end opening 164 of the external tube 160 through a conduit (not shown) formed inside the external tube 160. Thus, carbon dioxide supplied from a gas supply apparatus 66 to the gas supply port 162 is introduced into a digestive tract via the distal end opening 164 through the conduit inside the external tube 160.

According to the first variation, there is no need to use a forceps tube 96 that forms an internal conduit in the insertion part 12 of the endoscope 10 as a part of the gas supply conduit. This enables the forceps tube 96 to be used for other purposes.

[Second Variation]

Figure 12:
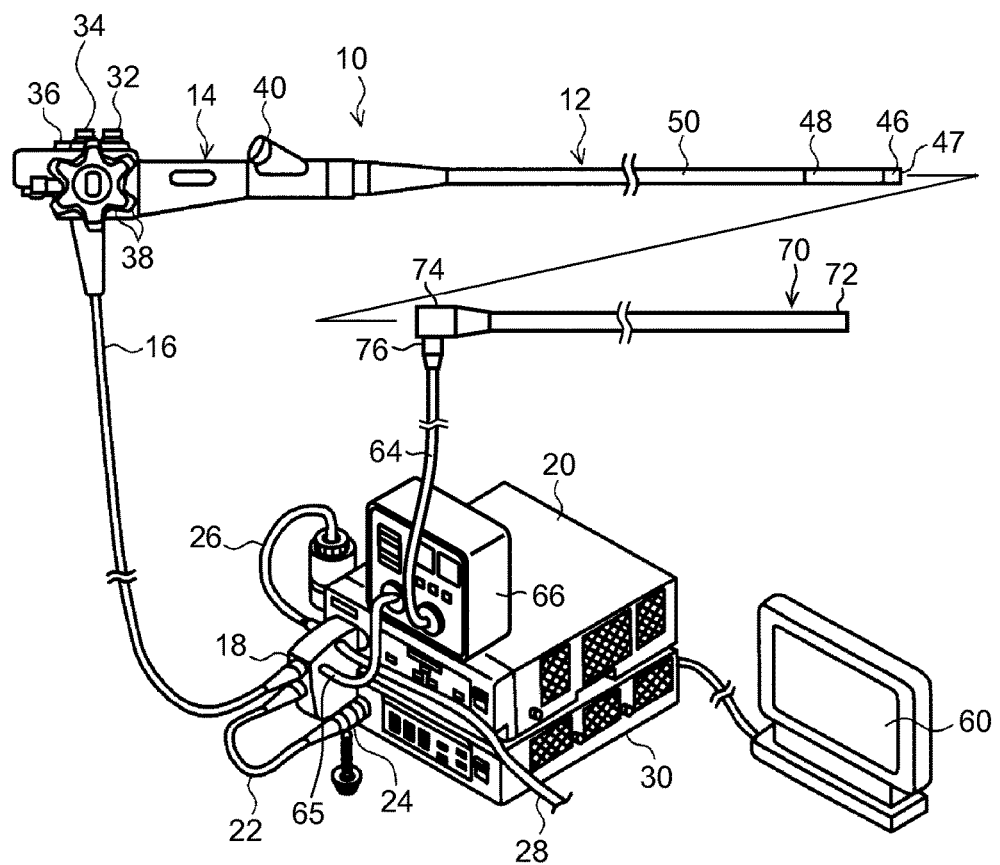
FIG. 12 is an overall configuration diagram illustrating a configuration outline of an endoscope system as a second variation.
Figure 13:
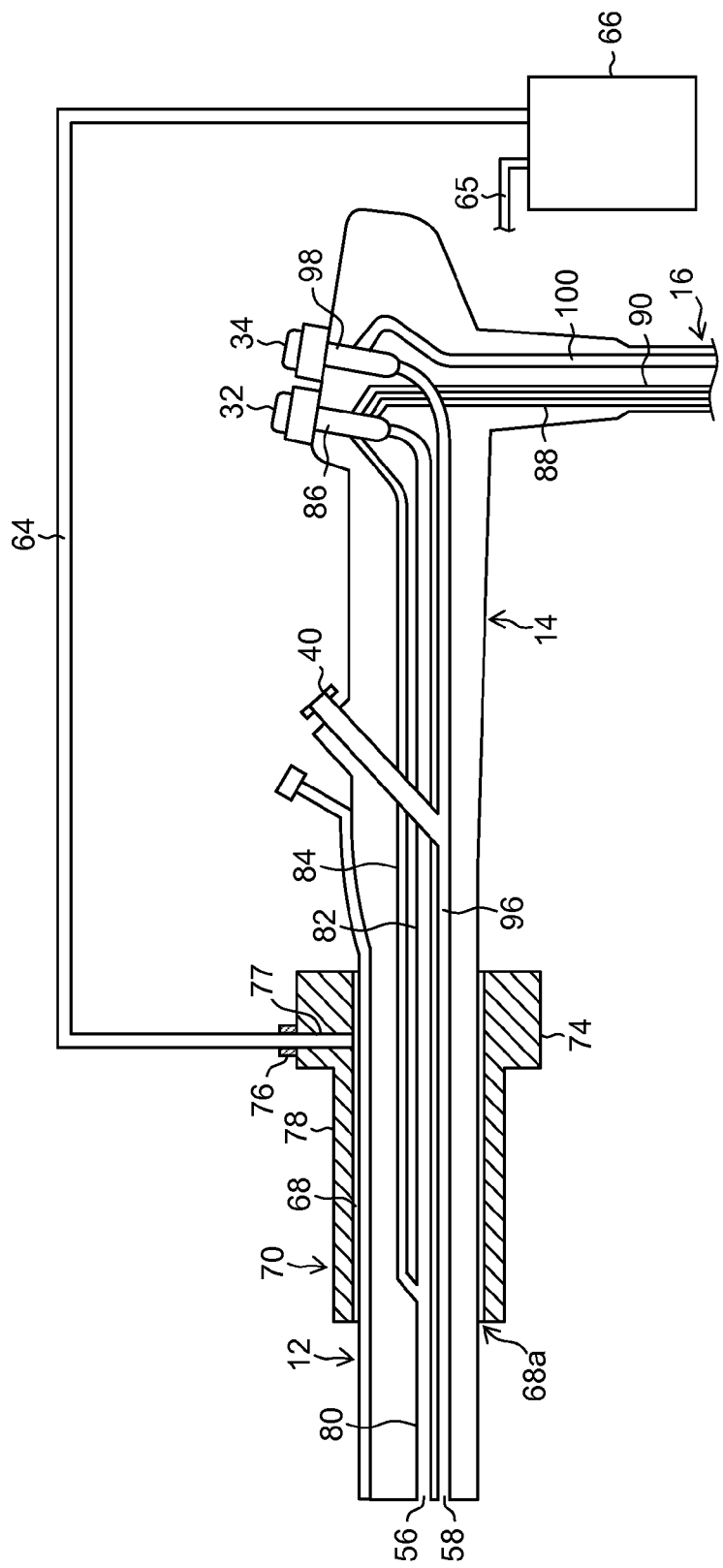
FIG. 13 is a conduit configuration diagram illustrating an internal configuration of the endoscope system shown in FIG. 12.

FIG. 12 is an overall configuration diagram illustrating configuration outline of an endoscope system as a second variation. FIG. 13 is a conduit configuration diagram illustrating n internal configuration of the endoscope system shown in FIG. 12. In FIGS. 12 and 13, members identical or similar to those of FIGS. 1 and 3 are assigned with the same reference numerals, and their descriptions are omitted.

As illustrated in FIGS. 12 and 13, in the second variation, a part of a gas supply conduit for supplying carbon dioxide into the digestive tract is constituted by an insertion channel 68 which is provided inside of an insertion aid 70 for guiding an insertion part 12 of an endoscope 10 into a digestive tract.

The insertion aid 70 is formed in a cylindrical shape, and has an inside diameter slightly larger than the outside diameter of the insertion part 12 with sufficient flexibility. At the base end of the insertion aid 70, a hard grip portion 74 is provided. The grip portion 74 permits the insertion of the insertion part 12.

On the outer circumference of the grip portion 74, a gas supply port 76 for the supply of carbon dioxide is provided. One end of a conduit 77 is connected to the gas supply port 76. The other end of the conduit 77 is open to the inner circumference of the insertion aid 70, and communicates with the insertion channel 68 formed inside the insertion aid 70.

One end of an automatic gas supply tube 64 is detachably connected to the gas supply port 76, and the other end of the automatic gas supply tube 64 is connected to a gas supply apparatus 66. Thus, carbon dioxide fed from the gas supply apparatus 66 is supplied to the insertion channel 68 through the conduit 77 via the gas supply port 76 and then introduced into a digestive tract via a distal end opening 68a of the insertion channel 68.

Also, although it is not shown, at the insertion channel 68 of the insertion aid 70, a valve member is provided as airtight keeping means which comes into close contact with the outer circumference of the insertion part 12 of the endoscope 10 and keeps airtightness in order to prevent carbon dioxide fed into the digestive tract from leaking outside the body via the insertion channel 68. This means that carbon dioxide supplied from the gas supply apparatus 66 to the insertion channel 68 inside the insertion aid 70 can be supplied into the digestive tract via the distal end opening 68a without leaking outside the body through the insertion channel 68.

According to the second variation, the insertion channel 68 formed inside the insertion aid 70 (to be specific, a gap formed between the inner wall of the insertion channel 68 and the insertion part 12) constitutes a part of the gas supply conduit for supplying carbon dioxide into the digestive tract. Thus, in like manner with the first variation, there is no need to use a forceps tube 96 that forms an internal conduit in the insertion part 12 of the endoscope 10 as a part of a gas supply conduit. Then this enables the forceps tube 96 to be used for other purposes.

[Third Variation]

Figure 14:
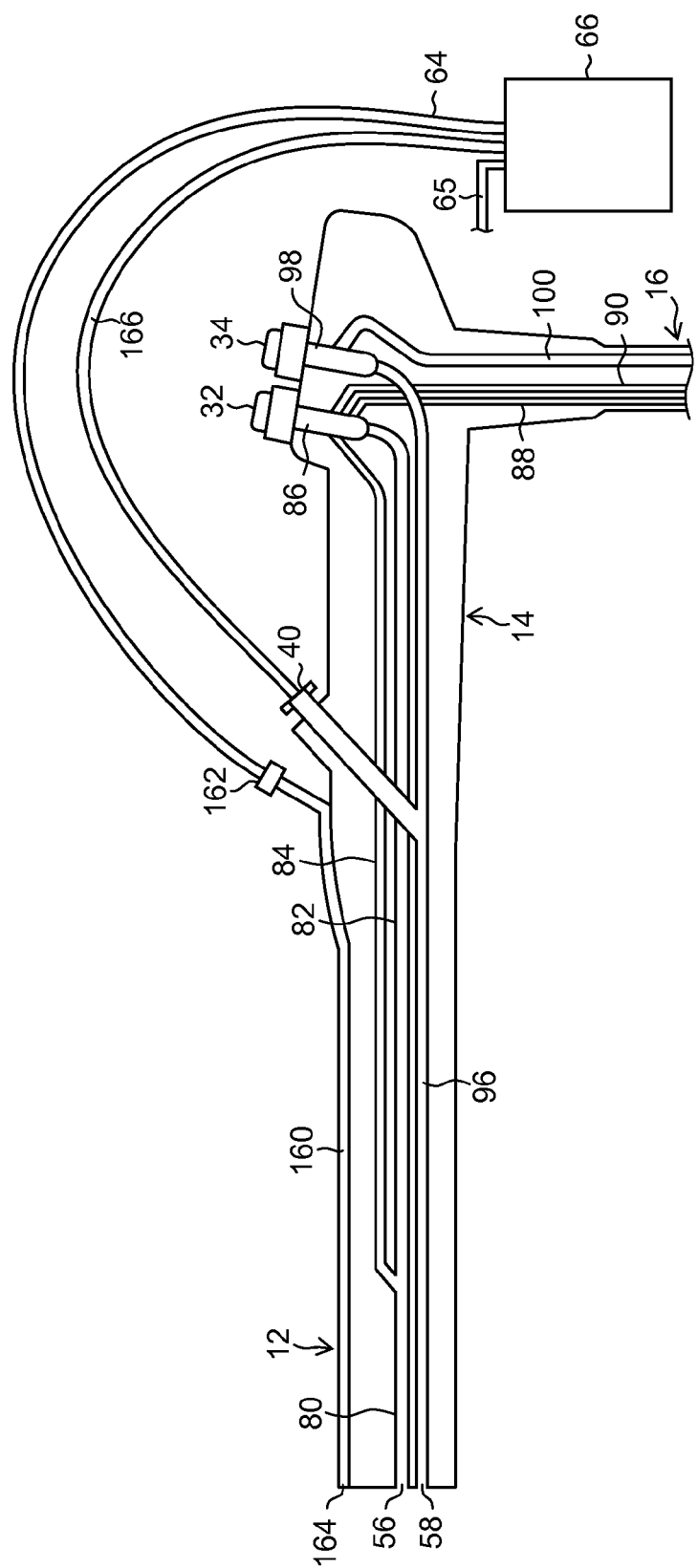
FIG. 14 is a schematic diagram schematically illustrating a conduit configuration of the endoscope as a third variation.
Figure 15:
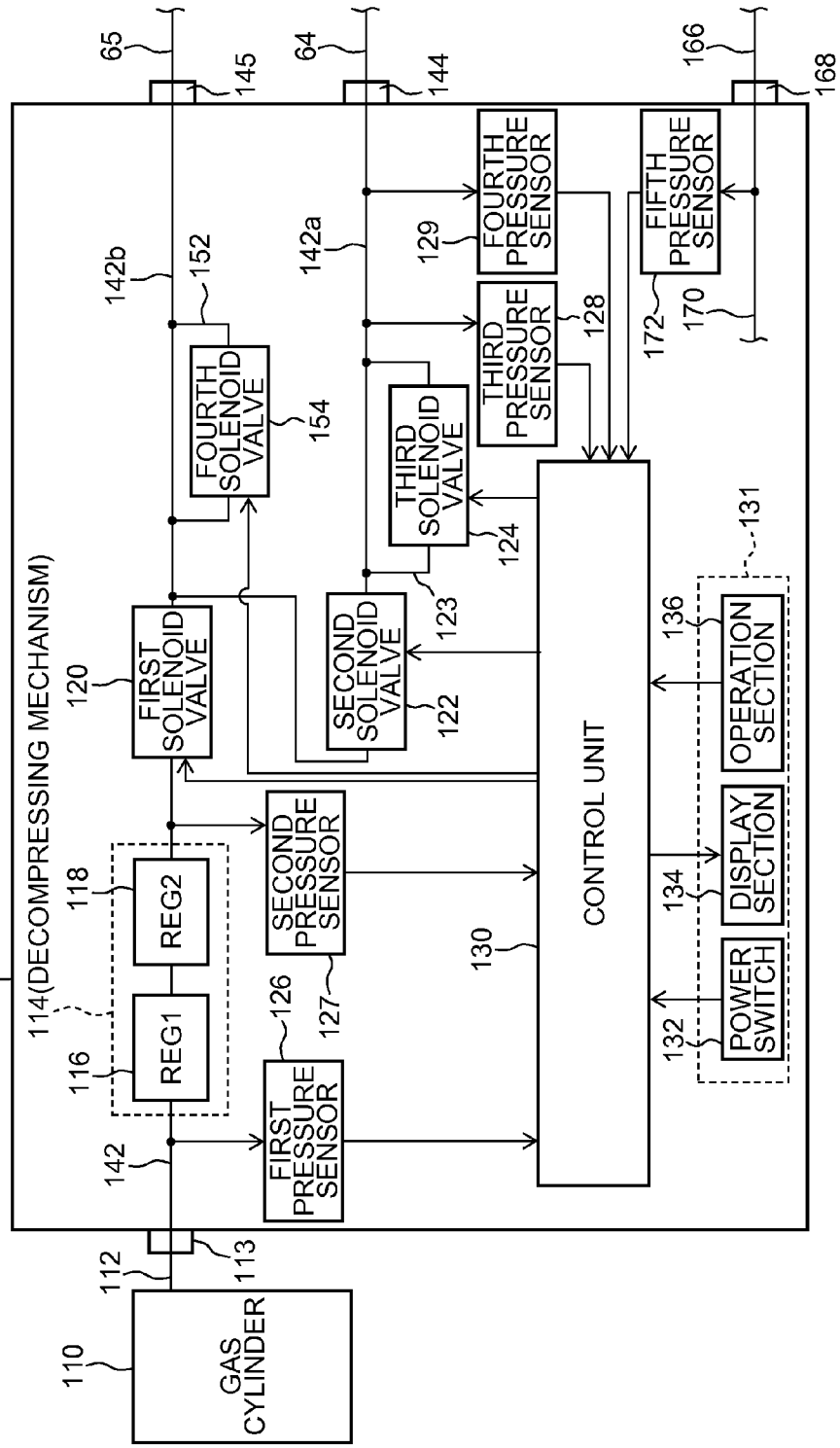
FIG. 15 is a block diagram illustrating a configuration of a gas supply apparatus as the third variation.

FIG. 14 is a schematic diagram schematically illustrating a conduit configuration of the endoscope as a third variation. FIG. 15 is a block diagram illustrating a configuration of a gas supply apparatus as the third variation. In FIGS. 14 and 15, members identical or similar to those of FIGS. 3 and 4 are assigned with the same reference numerals, and their descriptions are omitted.

The third variation is similar with the first variation in that an external tube 160, which is attached to the outside of an insertion part 12 of an endoscope 10 along the longitudinal direction of the insertion part 12, constitutes a part of a gas supply conduit. They are, however, different from each other in that the third variation includes a pressure detection conduit for detecting pressure in a digestive tract is constituted separately from the gas supply conduit described above.

Specifically, with reference to FIG. 14, one end of a pressure detection tube 166 is detachably connected to a forceps insertion opening 40 of the endoscope 10, and the other end of the pressure detection tube 166 is connected to a pressure detection connector 168 of a gas supply apparatus 66.

With reference to FIG. 15, an internal conduit 170 is provided inside the gas supply apparatus 66. The internal conduit 170 does not communicate with an internal conduit 142 and branch conduits 142a, 142b. One end of the internal conduit 170 is connected to the pressure detection connector 168. A fifth pressure sensor 172 is connected to the internal conduit 170. The fifth pressure sensor 172 detects pressure in a digestive tract via the pressure detection conduit (the internal conduit 170, the pressure detection tube 166 and a forceps tube 96) which is constituted separately from the gas supply conduit (the first branch conduit 142a, an automatic gas supply tube 64 and the external tube 160) for supplying carbon dioxide into the digestive tract.

According to the third variation, in a gas supply mode for FD/IBS diagnoses, the pressure in the digestive tract is detected via the pressure detection conduit constituted separately from the gas supply conduit for supplying carbon dioxide into the digestive tract. This enables the detection of the pressure in the digestive tract with stability and high accuracy without being affected by the supply of gas into the digestive tract. This allows pressure in the digestive tract to be adjusted to a target pressure with ease and high accuracy. Thus, diagnostic tests for functional dyspepsia (FD) and irritable bowel syndrome (IBS) can be performed easily and in detail.

Further, the third variation has shown an aspect in which the external tube 160 constitutes a part of the gas supply conduit and the forceps tube 96 constitutes a part of the pressure detection conduit. Applicable aspects, however, are not limited to this aspect. For example, an aspect in which the forceps tube 96 constitutes a part of the gas supply conduit and the external tube 160 constitutes a part of the pressure detection conduit, i.e. the inverse of the third variation aspect, can be used. In other words, one end of the automatic gas supply tube 64 and one end of the pressure detection tube 166 may be connected to the forceps insertion opening 40 and the gas supply port 162 of the external tube 160, respectively.

Also, when a plurality of treatment tool channels (treatment tool insertion channels) are provided at the insertion part 12 of the endoscope 10, one treatment tool channel may constitute a part of the gas supply conduit and the other treatment tool channel may constitute a part of the pressure detection conduit may be used.

Also, when an insertion aid 70 is used as in the case of the second variation, an insertion channel 68 inside the insertion aid 70 may constitute a part of the gas supply conduit and a forceps tube 96 that forms an internal conduit in an endoscope 10 may constitute a part of the pressure detection conduit may be used. Also, an inverse configuration to this may be used.

What is claimed is:

1. A gas supply apparatus comprising:
   a gas supply conduit to supply a gas to a digestive tract inside a subject;
   a pressure sensor which detects a pressure in the digestive tract via the gas supply conduit;
   a solenoid proportional valve which regulate an amount of the gas supplied to the digestive tract via the gas supply conduit; and
   a control unit which control operation of the solenoid proportional valve, wherein
   the control unit is configured to operate in:
   a first gas supply mode which is a gas supply mode for endoscopy, in which the control unit controls the solenoid proportional valve base on a detection result of the pressure sensor so that the pressure in the digestive tract becomes a set pressure; and
   a second gas supply mode which is a gas supply mode for the control unit being configured to estimate a capacity of the digestive tract based on a pressure in the digestive tract before gas is supplied to inside of the digestive tract and a pressure in the digestive tract after gas is supplied to inside of the digestive tract, and to execute diagnostic testing for functional dyspepsia or irritable bowel syndrome, in which the control unit controls the solenoid proportional valve according to a capacity of the digestive tract to supply a fixed amount of the gas into the digestive tract based on the estimated capacity of the digestive tract, and
   the control unit selectively switches between the first gas supply mode and the second gas supply mode.

2. The gas supply apparatus according to claim 1, wherein the control unit stores in a memory, data indicating correspondences among an amount of gas supplied into the digestive tract, a pressure change before and after gas is supplied in the digestive tract, and a capacity of the digestive tract capacity, and
   when estimating the capacity of the digestive tract, the control unit refers to the data in the memory.

3. The gas supply apparatus according to claim 1, wherein the fixed amount of the gas supplied into the digestive tract is 10% of the capacity of the digestive tract, or less.

4. The gas supply apparatus according to claim 1, further comprising
   an operation device which instructs execution of the supply of gas into the digestive tract,
   wherein in response to an operation on the operation device, the control unit switches to the second gas supply mode.

5. The gas supply apparatus according to claim 4, wherein the operation device is an operation button arranged on a front panel on a casing of the gas supply apparatus.

6. The gas supply apparatus according to claim 1, further comprising
   a display device which indicates the pressure in the digestive tract according to the result detected by the pressure sensor.

7. The gas supply apparatus according to claim 1, wherein the control unit stops the supply of the gas into the digestive tract when the pressure in the digestive tract exceeds a set pressure.

8. The gas supply apparatus according to claim 1, further comprising
   a setting device which sets the amount of the gas supplied into the digestive tract in the second gas supply mode.

9. The gas supply apparatus according to claim 1, further comprising
   a pressure detection conduit for detecting a pressure in the digestive tract, the pressure detection conduit which is separately constituted from the gas supply conduit,
   wherein the pressure sensor detects the pressure in the digestive tract through the pressure detection conduit.

10. The gas supply apparatus according to claim 1, wherein at least a part of the gas supply conduit is a conduit which is provided to an insertion part of an endoscope, an insertion aid for guiding the insertion part into a body cavity or an external instrument disposed along the insertion part.

* * * * *